(12) United States Patent
Kals

(10) Patent No.: US 9,084,894 B2
(45) Date of Patent: Jul. 21, 2015

(54) PROGRESSIVE PARAMETER SCAN FOR COCHLEAR IMPLANTS

(75) Inventor: Mathias Kals, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 339 days.

(21) Appl. No.: 13/478,424

(22) Filed: May 23, 2012

(65) Prior Publication Data
US 2012/0303095 A1    Nov. 29, 2012

Related U.S. Application Data

(60) Provisional application No. 61/489,345, filed on May 24, 2011.

(51) Int. Cl.
| | |
|---|---|
| *A61N 1/36* | (2006.01) |
| *A61B 5/04* | (2006.01) |
| *A61N 1/372* | (2006.01) |
| *A61B 5/00* | (2006.01) |
| A61B 5/0484 | (2006.01) |

(52) U.S. Cl.
CPC ........ *A61N 1/36032* (2013.01); *A61B 5/04001* (2013.01); *A61B 5/4836* (2013.01); *A61N 1/37241* (2013.01); *A61B 5/04845* (2013.01)

(58) Field of Classification Search
CPC ........... A61N 1/36032; A61N 1/37241; A61B 5/04001; A61B 5/4836; A61B 5/04845
USPC .......................................................... 607/57
See application file for complete search history.

(56) References Cited

U.S. PATENT DOCUMENTS

| | | | | |
|---|---|---|---|---|
| 6,157,861 | A * | 12/2000 | Faltys et al. ..................... | 607/57 |
| 2006/0235332 | A1 | 10/2006 | Smoorenburg .............. | 600/559 |
| 2007/0112395 | A1 | 5/2007 | Dijk et al. ........................ | 607/57 |
| 2007/0255344 | A1 | 11/2007 | Van Dijk ......................... | 607/57 |
| 2008/0319508 | A1 | 12/2008 | Botros et al. .................... | 607/57 |
| 2009/0254149 | A1 | 10/2009 | Polak .............................. | 607/57 |
| 2010/0268302 | A1 | 10/2010 | Botros ............................ | 607/57 |
| 2011/0082521 | A1 | 4/2011 | Botros et al. ................... | 607/57 |

OTHER PUBLICATIONS

International Searching Authority, International Search Report and Written Opinion, PCT/US2012/39064, date of mailing Sep. 6, 2012, 19 pages.

* cited by examiner

*Primary Examiner* — Mark W Bockelman
(74) *Attorney, Agent, or Firm* — Sunstein Kann Murphy & Timbers LLP

(57) ABSTRACT

A channel fitting process is described for a cochlear implant. A check is made for a channel fitting response condition to a stimulation signal, and if the condition is present, a channel operating parameter is set for the current electrode contact based on the channel fitting response condition, and if channel operating parameters have been set for all the electrode contacts, the channel fitting process ends. Otherwise, a next electrode contact is selected, the stimulation level is changed by a channel fitting increment, and if a stimulation level limit has been reached, the channel fitting process ends, or otherwise, the currently selected electrode contact is stimulated with the stimulation signal at the current stimulation level and the channel fitting process repeats.

16 Claims, 4 Drawing Sheets

PROGRESSIVE PARAMETER SCAN FOR COCHLEAR IMPLANTS

This application claims priority from U.S. Provisional Patent 61/489,345, filed May 24, 2011, which is incorporated herein by reference.

TECHNICAL FIELD

The present invention relates to medical implants, and more specifically to fit customization in audio prosthesis systems such as cochlear implant systems.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode contact can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode 1
$MCL_1$ (most comfortable loudness) for Electrode 1
Phase Duration for Electrode 1
$THR_2$ for Electrode 2
$MCL_2$ for Electrode 2
Phase Duration for Electrode 2
. . .
Pulse Rate
Number of fine structure channels
Compression
Parameters of frequency->electrode mapping
Parameters describing the electrical field distribution One common method for fit adjustment is to behaviorally find the threshold (THR) and most comfortable loudness (MCL) value for each separate electrode contact. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; and U.S. Patent Application 20060235332; which are incorporated herein by reference. Typically each stimulation channel is fitted separately without using the information from already fitted channels. The stimulation current on a given electrode typically is increased in steps from zero until the MCL or THR is reached.

One approach for an objective measurement of MCLs and THLs is based on the measurement of the ECAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation. This neural response is caused by the super-position of single neural responses at the outside of the axon membranes. The amplitude of the ECAP at the measurement position is typically in the ranges of μV. When performing objective measurements such as ECAP measurements in existing cochlear implant systems, usually each electrode contact of the implantable electrode array is scanned separately, increasing the stimulation signal current on an electrode contact in steps from zero or a very low level until an ECAP response is detected.

One major problem with these measurements can be the low success rate of measuring an ECAP on a specific electrode contact, in some cases as low as 20% (Brill et al., 2009). This low measurement success rate leads to a high potential risk of over-stimulation when a scan for ECAP thresholds is performed on a specific electrode contact without prior knowledge of MCL, since no exact stop criterion can be set. To determine ECAP levels without prior knowledge of MCL, an arbitrary predefined stop criterion is used. If the stop criterion for this is too conservative, then an existing ECAP threshold cannot be observed. And if the stop criterion is too progressive, then there may be a risk of over-stimulation when no ECAP response is observable on a specific electrode contact. The objectively measured ECAP threshold levels are usually somewhat lower than the behavioral MCL, so the potential risk of over-stimulation on the electrode contacts may be reduced if ECAP levels are observed and the scan is stopped. The definition of a universal stop criterion for all patients is not feasible since mean MCL values vary considerably between patients.

SUMMARY

Embodiments of the present invention are directed to determining cochlear implant operating parameters for electrode contacts in an implantable electrode array. A first electrode contact is stimulated with an initial stimulation signal at an initial stimulation level, and a channel fitting process is performed which includes: checking for a channel fitting response condition to the stimulation signal; if the channel fitting response condition is present: i. setting a channel operating parameter for the current electrode contact based on the channel fitting response condition and exclude current electrode contact from channel fitting process, and ii. if channel operating parameters have been set for all electrode contacts, ending the channel fitting process; otherwise, if the channel fitting response condition is not present or if channel operating parameters have not been set for all electrode contacts: i. selecting a next electrode contact, ii. changing the stimulation level by a channel fitting increment, iii. if a stimulation level limit has been reached, ending the channel fitting process, iv. otherwise, stimulating the currently selected electrode contact with the stimulation signal at the current stimulation level and continuing the channel fitting process.

In some embodiments, prior setting the channel operating parameter for the current electrode contact may include a refine measurement. This refine measurement includes: stimulating the current electrode contact with a stimulation signal at a stimulation level at which the current electrode contact was last stimulated where the channel fitting response condition was not fulfilled; checking for a refine measurement response condition to the stimulation signal, and if the refine measurement response condition is present: ending the refine measurement process on current electrode; otherwise: i. changing the stimulation level a refine measurement increment less or equal than the channel fitting increment, ii. if the stimulation level of the channel fitting process has been reached, ending the refine measurement process, iii. otherwise, stimulating the current electrode contact with the stimulation signal at the current stimulation level and repeating the refine measurement process.

The channel fitting process may be ended if the stimulation level becomes too loud for the implant patient. In some embodiments, the stimulation level limit may be a standard start value when the channel fitting process begins, and then reflect the channel operating parameters as they are set. The channel fitting increment and/or the refine measurement increment may be a level increase or a level decrease. The channel operating parameter may include an MCL stimulation level and/or a THR stimulation level. The channel fitting response condition and/or the refine measurement response condition may include presence of an electrically evoked compound action potential (ECAP), an electrical stapedius reflex threshold (ESRT), and/or an electrically evoked auditory brain stem response (EABR).

Embodiments also include a cochlear implant fitting system using a method according to any of the above, and a computer program product implemented in a computer readable storage medium for fitting an implanted electrode of a cochlear implant to an implanted patient and including program code for performing a method according to any of the above.

DETAILED DESCRIPTION

Embodiments of the present invention are directed to a progressive iterative method and a corresponding system for determining patient specific operating parameters for electrode contacts in a cochlear implant electrode array. A first electrode contact is stimulated with an initial stimulation signal at an initial stimulation level, and then an iterative channel fitting process is performed which includes all electrode contacts (channels) during the channel fitting process.

Figure 1:
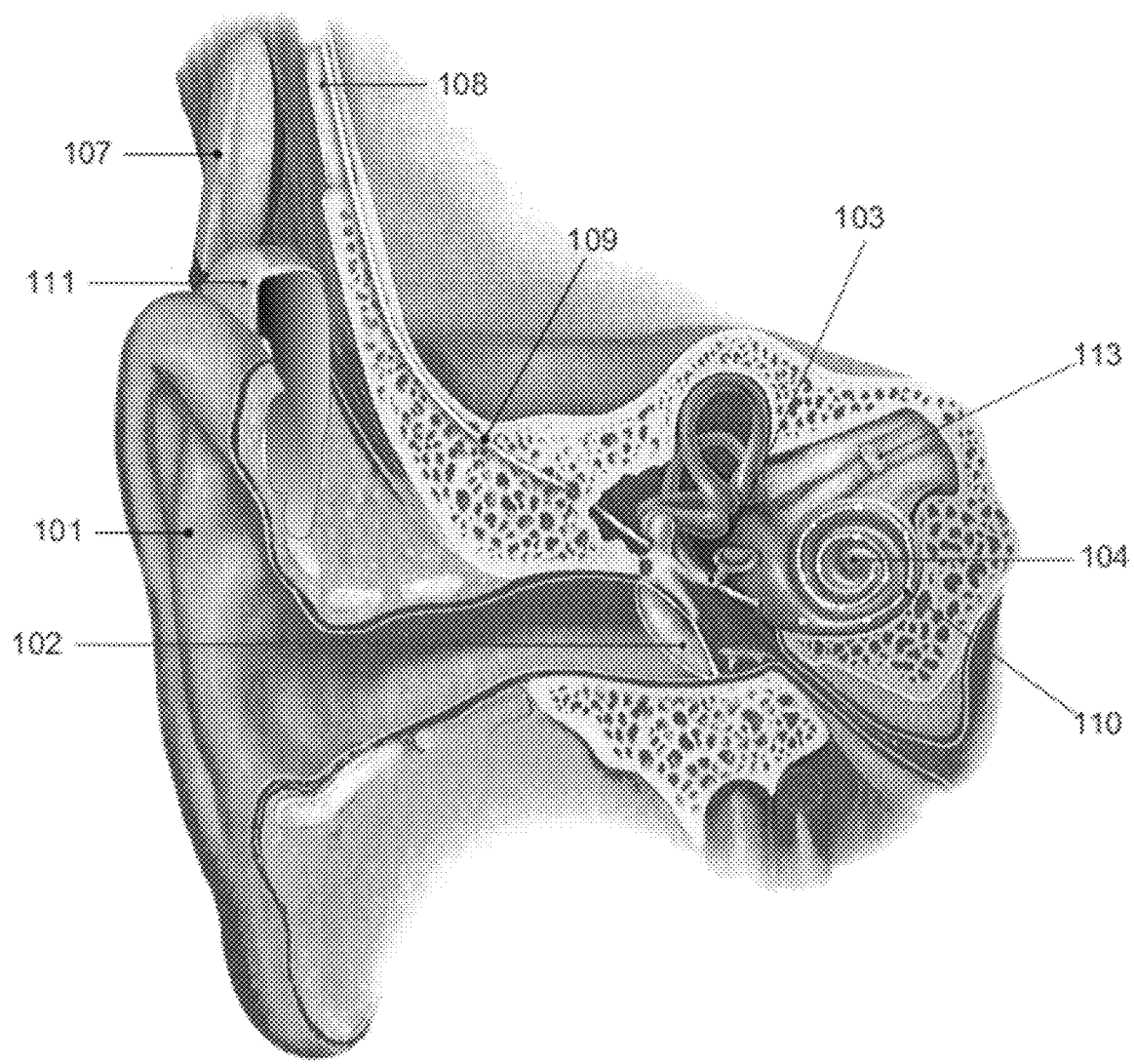
FIG. 1 shows anatomical structures in a human ear having a cochlear implant system.
Figure 2:
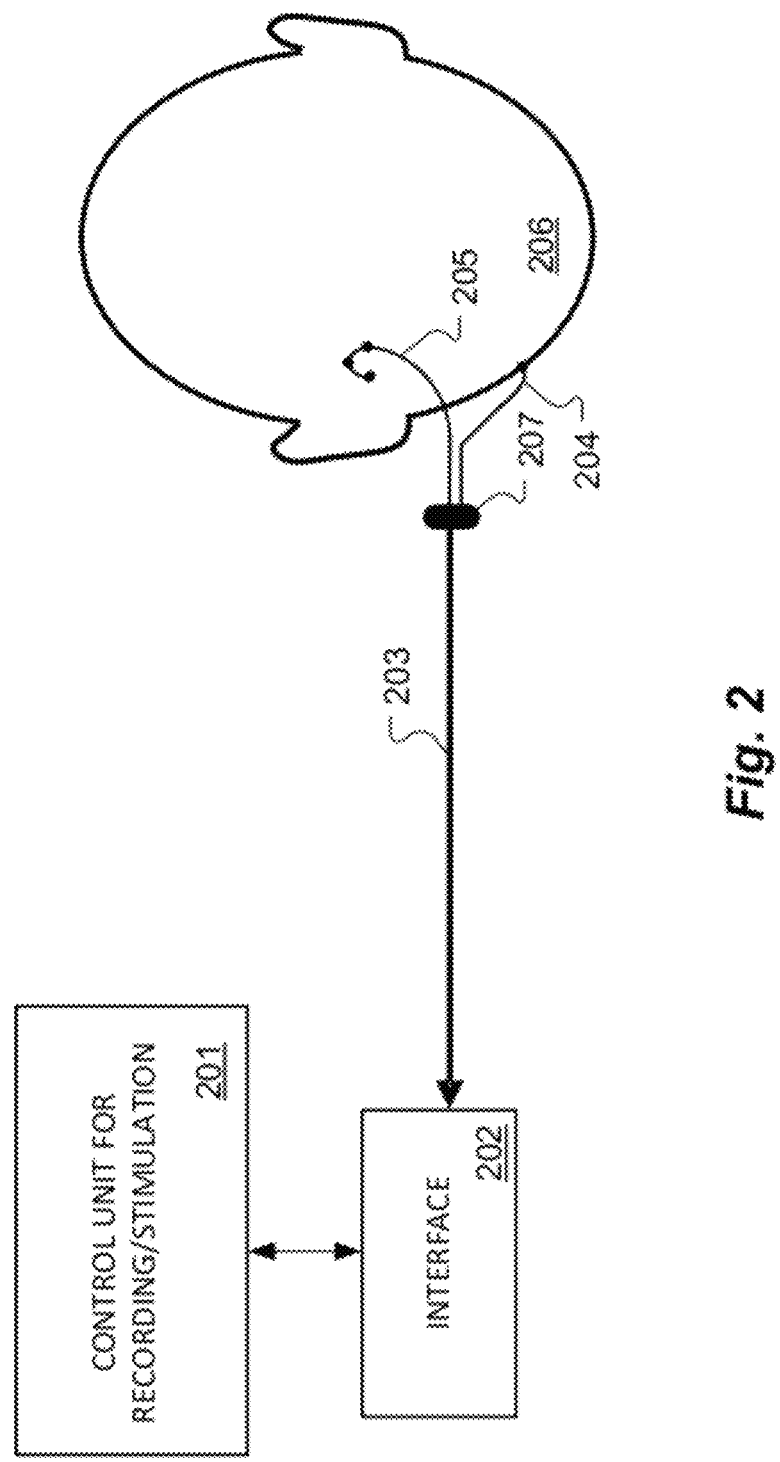
FIG. 2 shows a block diagram of a cochlear implant fitting system according to one specific embodiment of the present invention.

FIG. 2 shows a block diagram of a cochlear implant fitting system according to one specific embodiment of the present invention. Control Unit 201 for Recording and Stimulation, for example, a Med-El Maestro CI system, generates stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After delivering a stimulation pulse, a Cochlear Implant Electrode 204 may be used as a sensing element to determine current and voltage characteristics of the adjacent tissue.

Figure 3:
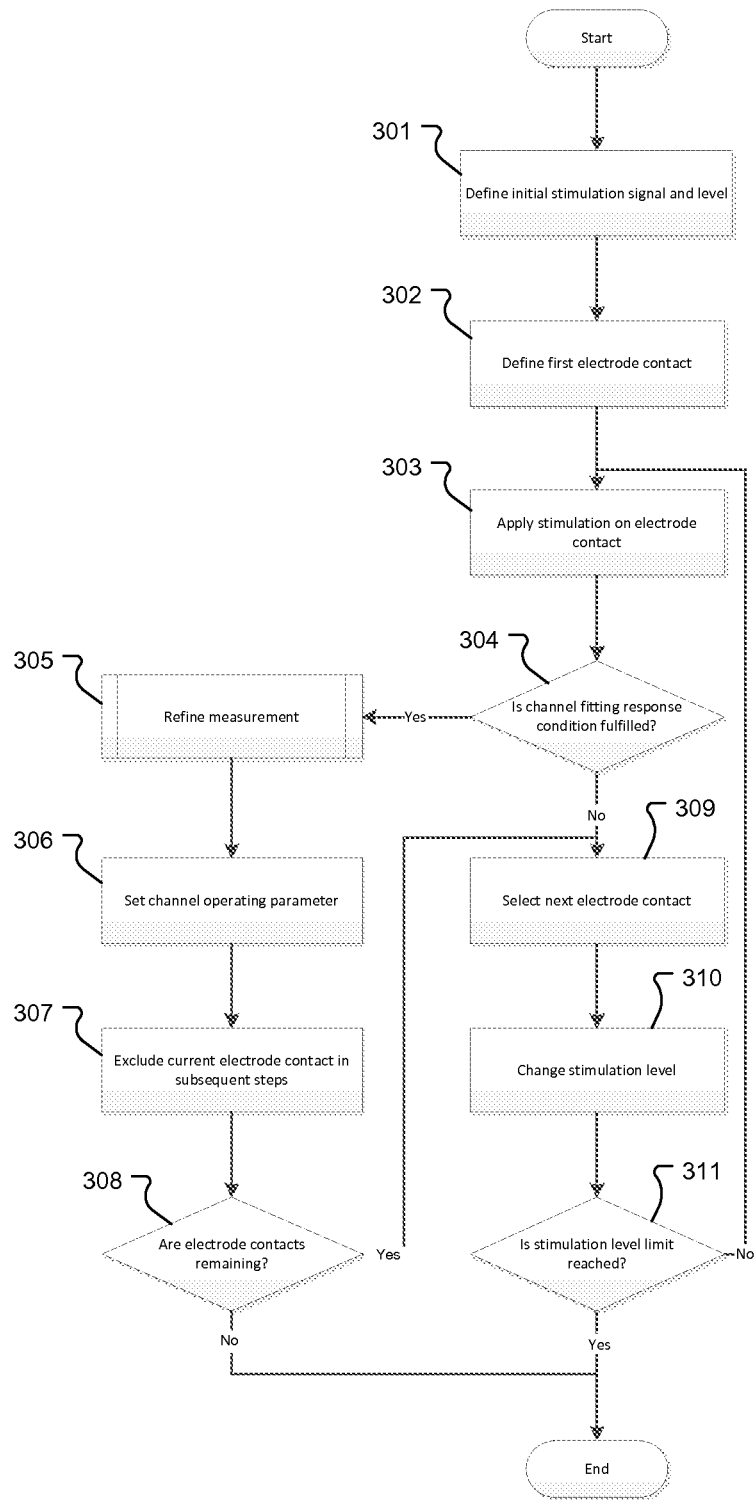
FIG. 3 shows various steps in an iterative channel fitting process according to an embodiment of the present invention.

FIG. 3 shows various logical steps in an algorithm for determining cochlear implant operating parameters for each electrode contact. First, an initial stimulation level is defined, step 301, and a first electrode contact selected, step 302. The first electrode contact is then stimulated with an initial stimulation signal at the initial stimulation level, step 303, and an iterative channel fitting process is begun wherein the electrode contacts are continuously switched during the channel fitting process.

After the electrode contact is stimulated, a check is made looking for a channel fitting response condition to the stimulation signal, step 304. For example, the channel fitting response condition may include presence of an electrically evoked compound action potential (ECAP), an electrical stapedius reflex threshold (ESRT), and/or an electrically evoked auditory brain stem response (EABR). If the channel fitting response condition is present, some embodiments may next perform a further refine measure process, step 305, described below. Based on the channel fitting response condition, a channel operating parameter for the current electrode contact is then set, step 306 (e.g., ECAP, MCL and/or THR) and that electrode contact is then removed from the remainder of the fitting process, step 307. If channel operating parameters have been set for all electrode contacts, step 308, the channel fitting process ends. Otherwise, if the channel fitting response condition is not present or if channel operating parameters have not been set for all electrode contacts, then a next electrode contact is selected, step 309, and the stimulation level is adjusted by a channel fitting increment, step 310, for example, by a step change increase or decrease. If this then results in a stimulation level limit being reached, step 311, the channel fitting process ends. Otherwise, the channel fitting process continues with stimulating the currently selected electrode contact with the stimulation signal at the current stimulation level, step 303.

In a progressive iterative channel fitting process, the channel fitting parameters (e.g., ECAP levels) are determined by scanning by a stepwise increment change and alternating switch of the N electrode contacts (channels) where the stimulation signal is applied. So in such a scan, a maximum overshoot $O_{max}$ by the use of a step size S can occur on a given electrode contact of:

$$O_{max}=(N-1)*S. \qquad \text{(Equ. 1)}$$

The maximum number of required steps $M_{max}$ for the iterative channel fitting process for an implant with levels $L_n$ can be calculated by:

$$M_{max}=\text{ceil}(\max(L_n)/S)+(N-1). \qquad \text{(Equ. 2)}$$

Figure 4:
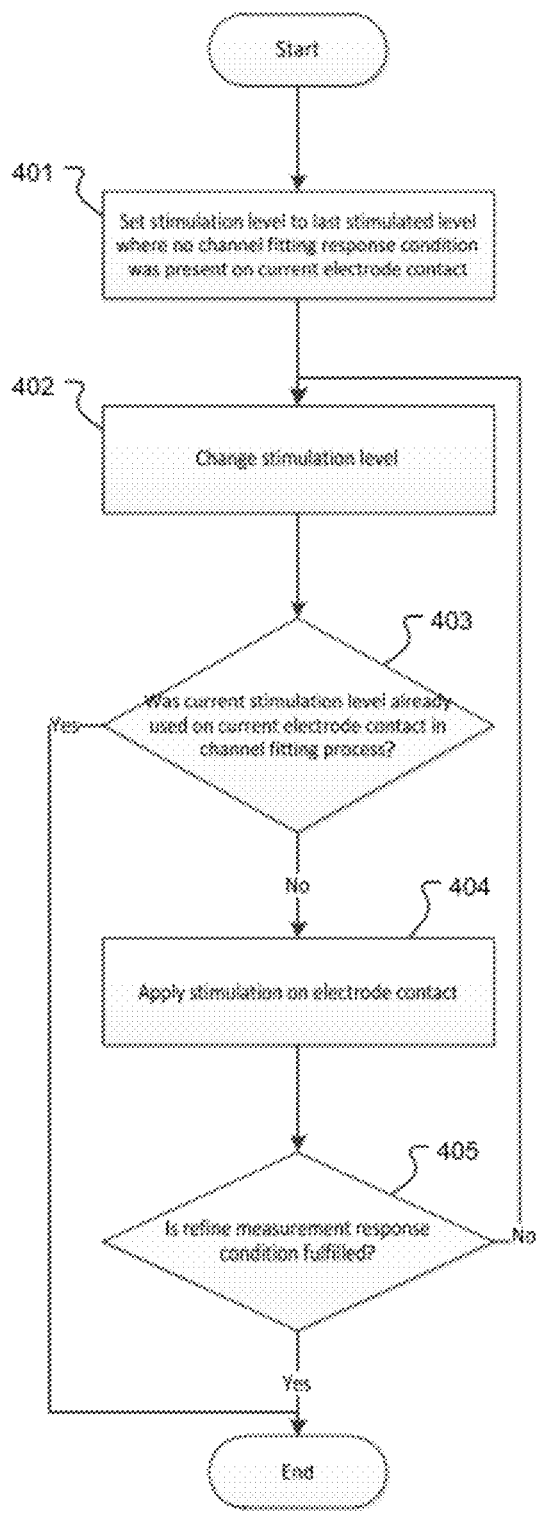
FIG. 4 shows various steps in an iterative refine measurement process according to an embodiment of the present invention.

In some embodiments, setting the channel operating parameter for the current electrode contact may include performing a refine measurement process, step 305. FIG. 4 shows one example of such a refine measurement process which starts with setting the stimulation level for the current electrode contact to its last previous level for which no channel fitting response condition was present, step 401. From this initial refine measurement stimulation level, the stimulation level is then adjusted by a refine measurement increment (which is less than or equal to the channel fitting increment), step 402, for example, by a step increase or decrease. If the stimulation level of the channel fitting process has been reached, step 403, the refine measurement process ends. Otherwise, the currently selected electrode contact is stimulated with the stimulation signal at the current stimulation level, step 404. If a refine measurement response condition is present, the channel operating parameter for the current electrode contact is then set based on the refine measurement response condition, and the refine measurement process ends, step 405 Otherwise, the refine measurement process iteratively repeats starting with changing the stimulation level a refine measurement increment, step 402.

More specifically, after detecting an ECAP response on a given electrode contact, the optional refine measurement process changes the stimulation level in steps of $S_F$ beginning from the last measured level of the selected electrode contact n, until a refine measurement response condition is present or the stimulation level is reached where a channel fitting response condition was already present. The channel fitting step size S and the refine measurement step size $S_F$ can be set differently ($S \geq S_F$). The maximum number of required steps $M_{F,max}$ for the refinement measurements in an electrode-array of N channels can be calculated by:

$$M_{F,max}=\text{ceil}((N^2-N(N+1)/2)*(S_F/S)) \qquad \text{(Equ. 3)}$$

This would result for example in a proportion of required scanning steps relative to the traditional method (number of traditional steps $M_T$, where a step size of S is used) of about $(M_{max}+M_{F,max})/M_T=0.12$ when a charge of $L_n=10$ nC for ECAP levels and a step size $S=S_F=0.05$ nC is assumed for a N=12 channel implant.

In some embodiments, the stimulation level in the channel fitting process may only be incremented when no response condition was present. This less progressive scan could lead to a smaller overshoot $O_{max}$ and faster scan if nearly equal target levels across all channels are present. Based on the already determined channel operating parameters and/or statistical analysis of ECAP, MCL and THR data, the stop criterion, stimulation level limit, can be calculated continuously.

The consecutive increase of stimulation level while switching channels/electrode contacts leads to a fast and effective determination of any detectable ECAP level or any objective or behavioural level of an electrode array. The same general approach can also be used for scanning other objective levels (e.g., ESRT and EABR) and/or behavioural levels (e.g., THR and MCL). For determining louder levels such as MCL, the step size may need to be set accordingly so that the desired level plus the maximum possible overshoot $O_{max}$ does not reach uncomfortable loudness (UCL) to avoid uncomfortable loud stimulation during channel fitting process (for example $MCL+O_{max}<UCL$).

Especially for ECAP measurements where in some cases the success rate can be as low as p=0.2, it can be difficult using prior techniques to decide when the first electrode contact is measured if the target electrode contact delivers no response or the applied stimulation signal is too low. Consequently an arbitrary conservative predefined stop criterion is applicable, which can lead to false negative results. However, when all channels N=12 are considered as is done in embodiments here, the probability of observing at least one ECAP response can be calculated based on the binomial distribution B(n, p):

$$P(X\geq 1)=1-P(X=0)=1-B(0|12, 0.2) \qquad \text{(Equ. 4)}$$

A calculation with Equation 4 yields a probability of p=0.93 that at least one observable ECAP will be successfully measured across the full electrode array if a minimum success rate of p=0.2 is assumed for each electrode contact. This would allow following a more progressive stop criterion for measurements until the first response is measured. For the subsequent measurements, a more accurate stop criterion than a predefined stop criterion can be utilized which is based on the already observed response and which considers statistical properties of ECAP or MCL values (e.g. 95% confidence interval). This would limit the risk of over-stimulation and false negative rate while scanning for responses.

Thus embodiments of the present invention provide a fast, safe and efficient method to determine ECAP levels. The operating parameter levels of all the electrode contacts on the entire electrode array can be determined with considerably fewer steps (typically only about 12% are required) in behavioural as well as in objective parameter measurements, in comparison to prior art. This approach also may be more accurate than a prior art fitting procedure where only a subset of widely spaced electrode contacts are measured and the residual ones are linearly interpolated. Nevertheless, in some embodiment both methods may be combined. Some embodiments can also use a top-down procedure where the scan starts from a defined upper limit and is performed by decreasing levels.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for determining cochlear implant operating parameters for a plurality of electrode contacts in an implantable electrode array, the method comprising:
   stimulating a first electrode contact with an initial stimulation signal at an initial stimulation level; and
   performing a channel fitting process including:
      checking for a channel fitting response condition to the stimulation signal;
      when the channel fitting response condition is present:
         i. setting a channel operating parameter for the selected electrode contact based on the channel fitting response condition and completing the channel fitting process for the selected electrode contact, and
         ii. if channel operating parameters have been set for all electrode contacts, ending the channel fitting process;
      and when the channel fitting response condition is not present or when channel operating parameters have not been set for all electrode contacts:
         iii. selecting a next electrode contact,
         iv. changing the stimulation level by a channel fitting increment,
         v. if a stimulation level limit has been reached, ending the channel fitting process,
         vi. otherwise, stimulating the selected electrode contact with the stimulation signal at the current stimulation level and repeating the channel fitting process.

2. A method according to claim 1, wherein before setting the channel operating parameter for the selected electrode contact, a refine measurement process is performed including:
   stimulating the selected electrode contact with a stimulation signal at a stimulation level at which the current electrode contact was last stimulated where no channel fitting response condition was present; and
   checking for a refine measurement response condition to the stimulation signal if the refine measurement response condition is present, ending the refine measurement process, and otherwise:
      i. changing the stimulation level a refine measurement increment less than or equal to the channel fitting increment,
      ii. if the stimulation level limit has been reached, ending the refine measurement process,
      iii. otherwise, stimulating the current electrode contact with the stimulation signal at the current stimulation level and repeating the refine measurement process.

3. A method according to claim 2, wherein the refine measurement increment is a level increase.

4. A method according to claim 2, wherein the refine measurement increment is a level decrease.

5. A method according to claim 2, wherein the refine measurement response condition and the channel fitting response condition are the same.

6. A method according to claim 2, wherein the refine measurement response condition and the channel fitting response condition are different.

7. A method according to claim 1, wherein performing the channel fitting process includes ending the process if the stimulation level reaches an uncomfortable loudness (UCL).

8. A method according to claim 1, wherein the stimulation level limit is a standard start value when the channel fitting process begins, and then reflects the channel operating parameters as they are set.

9. A method according to claim 1, wherein the channel fitting increment is a level increase.

10. A method according to claim 1, wherein the channel fitting increment is a level decrease.

11. A method according to claim 1, wherein the channel operating parameter includes a most comfortable loudness (MCL) stimulation level.

12. A method according to claim 1, wherein the channel operating parameter includes a threshold (THR) stimulation level.

13. A method according to claim 1, wherein the channel fitting response condition includes presence of an electrically evoked compound action potential (ECAP).

14. A method according to claim 1, wherein the channel fitting response condition includes presence of an electrical stapedius reflex threshold (ESRT).

15. A method according to claim 1, wherein the channel fitting response condition includes presence of an electrically evoked auditory brain stem response (EABR).

16. A cochlear implant system fit to an implanted patient using the method according to any of claims 1-15.

* * * * *